US008829134B2

(12) United States Patent  (10) Patent No.: US 8,829,134 B2
Heilek et al.  (45) Date of Patent: Sep. 9, 2014

(54) PROCESS FOR TRANSPORTING IN THE TANK OF A TANK TRUCK OR TANKER SHIP A LIQUID MONOMER PHASE WITHDRAWN FROM A STORAGE VESSEL

(75) Inventors: Joerg Heilek, Bammental (DE); Ulrich Hammon, Mannheim (DE); Volker Schliephake, Schifferstadt (DE); Klaus Joachim Mueller-Engel, Stutensee (DE); Till Blum, Speyer (DE)

(73) Assignee: BASF SE, Ludwigshafen (DE)

( * ) Notice: Subject to any disclaimer, the term of this patent is extended or adjusted under 35 U.S.C. 154(b) by 959 days.

(21) Appl. No.: 12/053,158

(22) Filed: Mar. 21, 2008

(65) Prior Publication Data

US 2008/0234446 A1  Sep. 25, 2008

Related U.S. Application Data

(60) Provisional application No. 60/896,582, filed on Mar. 23, 2007.

(30) Foreign Application Priority Data

Mar. 23, 2007 (DE) .......................... 10 2007 014 603

(51) Int. Cl.
  C08F 2/00 (2006.01)
  B01D 37/00 (2006.01)
  C07C 67/56 (2006.01)
  C07C 67/62 (2006.01)
  C07C 51/42 (2006.01)
  C07C 51/47 (2006.01)
  C07C 45/78 (2006.01)
  C07C 45/79 (2006.01)
  C07C 51/50 (2006.01)

(52) U.S. Cl.
  CPC .............. *C07C 45/79* (2013.01); *C07C 67/56* (2013.01); *C07C 67/62* (2013.01); *C07C 51/42* (2013.01); *C07C 51/47* (2013.01); *C07C 45/78* (2013.01); *C07C 51/50* (2013.01)
  USPC .......... 526/317.1; 526/68; 210/767; 562/598; 562/600

(58) Field of Classification Search
  USPC ........... 562/598, 600; 526/317.1, 68; 210/767
  See application file for complete search history.

(56) References Cited

U.S. PATENT DOCUMENTS

| 4,435,556 | A | * | 3/1984 | Masler, III | ..................... 252/180 |
| 5,637,222 | A | | 6/1997 | Herbst et al. | |
| 6,504,056 | B2 | * | 1/2003 | Aichinger et al. | ............ 562/600 |
| 6,910,511 | B2 | | 6/2005 | Yada et al. | |
| 2002/0008064 | A1 | * | 1/2002 | Hamamoto et al. | .......... 210/435 |
| 2004/0242826 | A1 | | 12/2004 | Nishimura | |
| 2007/0173665 | A1 | | 7/2007 | Ueno et al. | |
| 2007/0173666 | A1 | * | 7/2007 | Ishii et al. | ..................... 562/600 |

FOREIGN PATENT DOCUMENTS

| DE | 2 246 480 | 4/1974 |
| DE | 2 362 373 | 7/1974 |
| DE | 195 01 325 | 7/1996 |
| DE | 196 31 645 | 2/1998 |
| DE | 198 38 845 | 3/2000 |
| DE | 199 24 533 | 11/2000 |
| DE | 102 19 089 | 11/2002 |
| DE | 103 36 386 | 3/2004 |
| DE | 10 2004 034 515 | 2/2006 |
| EP | 0 695 736 | 2/1996 |
| EP | 0 784 046 | 7/1997 |
| EP | 0 792 867 | 9/1997 |
| EP | 0 982 287 | 3/2000 |
| EP | 0 982 288 | 3/2000 |
| EP | 0 982 289 | 3/2000 |
| EP | 1 041 062 | 10/2000 |
| EP | 1 097 741 | 5/2001 |
| EP | 1 125 912 | 8/2001 |
| EP | 1 361 203 | 11/2003 |
| EP | 1 388 533 | 2/2004 |
| EP | 1 695 954 | 8/2006 |
| JP | 05-246942 | 9/1993 |
| JP | 09-227586 | 9/1997 |
| JP | 2001-233820 | 8/2001 |
| JP | 2003-183218 | 7/2003 |
| JP | 2003-231663 | 8/2003 |
| JP | 2003-287200 | 10/2003 |
| JP | 2004-528370 | 9/2004 |
| JP | 2005-239656 | 9/2005 |
| JP | 2007-191449 | 8/2007 |
| SU | 162835 | 5/1964 |

(Continued)

OTHER PUBLICATIONS

Research Disclosure Database No. 513001, Jan. 2007—PF 58405 (English Text attached).
Research Disclosure Database No. 513002, Jan. 2007—PF 58406 (English Text attached).
Communication dated Jan. 26, 2012 concerning third-party observation made in JP Application No. 2010-500205.
Chemical Products of 15107, Kagaku Kogyo Nippo Sha, pp. 348-351 and 365-368, Jan. 23, 2007.

*Primary Examiner* — Ling Choi
*Assistant Examiner* — Chun-Cheng Wang
(74) *Attorney, Agent, or Firm* — Oblon, Spivak, McClelland, Maier & Neustadt, L.L.P.

(57) ABSTRACT

A process for transporting a liquid monomer phase which has been withdrawn from a storage vessel and comprises methacrylic monomers to an extent of ≥90% by weight, in a tank truck or in a tanker ship, in which the liquid monomer phase is subjected to a separating operation on the route from the storage vessel into the tank of a tank truck or of a tanker ship in order to separate polymer of the monomer present in dissolved form in the liquid monomer phase.

13 Claims, No Drawings

(56) References Cited

FOREIGN PATENT DOCUMENTS

| WO | WO 00/45928 | 8/2000 |
| WO | WO 01/96271 | 12/2001 |
| WO | WO 02/076917 | 10/2002 |
| WO | WO 2004/007405 | 1/2004 |
| WO | WO 2004/035514 | 4/2004 |
| WO | WO 2005/049543 | 6/2005 |
| WO | WO 2006/008083 | 1/2006 |

* cited by examiner

PROCESS FOR TRANSPORTING IN THE TANK OF A TANK TRUCK OR TANKER SHIP A LIQUID MONOMER PHASE WITHDRAWN FROM A STORAGE VESSEL

The present invention relates to a process for transporting a liquid monomer phase which has been withdrawn from a storage vessel and whose content of the monomer is ≥90% by weight in the tank of a tank truck or of a tanker ship, the monomer being a monomer from the group consisting of acrolein, methacrolein, acrylic acid, methacrylic acid, esters of acrylic acid and an alcohol having from 1 to 12 carbon atoms and esters of methacrylic acid and an alcohol having from 1 to 12 carbon atoms.

According to the above remarks, the term monomer(s) in this document includes acrolein, methacrolein, acrylic acid, methacrylic acid, esters of acrylic acid and an alcohol having from 1 to 12 carbon atoms and esters of methacrylic acid and an alcohol having from 1 to 12 carbon atoms. Useful alcohols include both monohydric alcohols (have one —OH group) and polyhydric alcohols (have more than one —OH group). These alcohols include in particular mono- and polyhydric alkanols having from 1 to 12, preferably from 1 to 8, carbon atoms.

This definition does not necessarily imply that the above-mentioned esters must be prepared by reaction of the corresponding alcohols with the particular acid. Instead, useful preparation processes are also other reactions, for example transesterifications or addition reactions.

Exemplary monomers include methyl acrylate, ethyl acrylate, n-butyl acrylate, isobutyl acrylate, tert-butyl acrylate, 2-ethylhexyl acrylate, hydroxyethyl acrylate, hydroxypropyl acrylate, hydroxymethyl methacrylate, hydroxypropyl methacrylate, 2-propylheptyl acrylate, methyl methacrylate, ethyl methacrylate, n-butyl methacrylate and tert-butyl methacrylate.

Typically, monomers are obtained by chemical synthesis.

However, they are not obtained immediately in pure form but rather as a constituent of gaseous or liquid product mixtures from which they have to be removed. This removal is generally undertaken using thermal separating processes, for example absorption, desorption, fractional condensation, extraction, crystallization, adsorption, etc., or using combinations of different such thermal separating processes (cf., for example, DE-A 19 924 533, WO 2004/035 514, EP-A 1 388 533, EP-A 778 225, EP-A 1 041 062, EP-A 982 287, EP-A 982 288, WO 01/96 271, DE-A 10 336 386, DE-A 19 631 645, DE-A 19 501 325, EP-A 982 289, DE-A 19 838 845, WO 02/076 917, EP-A 1 695 954, EP-A 695 736, EP-A 778 225, EP-A 1 041 062, US 2004/0 242 826, EP-A 792 867, EP-A 784 046, EP-A 695 736, EP-A 112 5912, EP-A 1 097 741, WO 00/45 928, DE-A 2 246 480, DE-A 2 362 373, U.S. Pat. No. 5,637,222 and the prior art cited in these documents).

The intermediate product or the pure product obtained is generally a liquid monomer phase whose content of the particular monomer is ≤90% by weight or ≥95% by weight.

Frequently, the last step on the route from the product mixture to the intermediate or pure product consists of a condensation out of a gaseous phase or of the melting of a crystalline phase. For example, the condensation can be effected in a rectification column above the feed point of the mixture to be separated (in the rectification column) into the rectification column out of the vapors ascending in the rectification column, and the pure product can be withdrawn from the rectification column above the aforementioned feed. The mixture to be separated can be fed into the rectification column either in liquid form (rectification) or in gaseous form (fractional condensation).

In both cases, i.e. both when the liquid monomer phase is obtained by condensation out of a gaseous phase and when the liquid monomer phase is obtained by melting a crystalline phase (from the crystals), it is normally obtained free of solids on visual inspection (i.e. when viewed with the naked human eye). The liquid monomer phase typically comprises free-radical polymerization inhibitors (inhibitors for suppressing undesired free-radical polymerization), which are regularly metered in in the course of its generation and/or as the completion of such a generation. In the case of generation by melting a crystalline phase, the polymerization inhibitor system may also already be present in the crystalline phase.

In principle, however, a liquid monomer phase which is an intermediate or pure product and contains the respective monomer at ≥90% by weight or ≥95% by weight can also be withdrawn from a separation column (a rectification column for example) below the feed point into the separation column (into the rectification column for example) of the mixture to be separated in a separation column (in a rectification column for example). For example, such a removal can also take place from the bottom region of the separation column (a rectification column for example). This will be the case for example when the monomer (acrylic acid for example) is absorbed from a product gas mixture of its production (for example acrylic acid) from the product gas mixture of a heterogeneously catalyzed partial gas phase oxidation of a $C_3$ precursor of acrylic acid (for example propylene, propane, glycerol, acrolein) with a liquid (for example water or aqueous solutions in the case of acrylic acid) which under standard conditions (25° C., 1 bar) boils at a lower boiling point than the monomer (acrylic acid for example) and the more volatile absorption liquid is subsequently separated rectificatively (if appropriate with the aid of an azeotropic entraining agent) from the absorbate (although frequently a liquid monomer phase described at the beginning remains behind).

The liquid monomer phases obtainable as described, being an intermediate or pure product, are normally fed to a storage vessel. If the liquid monomer phase by virtue of its process of production contains undissolved, visually visible polymer (the monomers relevant according to the present invention are all known to be prone, in an undesirable manner, to free-radical polymerization; the latter can be induced for example by light, temperature and/or impurities and is not completely avoidable even by the addition of inhibitors capable of suppressing such free-radical polymerizations to a certain extent; the production of the liquid monomer phases normally takes place in the presence of such polymerization inhibitors, which is why the liquid monomer phases generally contain such as a consequence of their process of production), it is generally separated off before the liquid monomer phase is transferred into the storage vessel. Such removal of undissolved solids is simple to accomplish by filtration by means of filters of appropriate mesh size.

Typically, such storage vessels are also referred to as a tank or else as a storage tank. The internal volume of a storage tank (which is typically at rest) occupiable by a liquid phase is generally from 100 m³ to 10 000 m³, frequently from 200 m³ to 1000 m³ and characteristically 500 m³ (cf., for example, Research Disclosure Database Number 513001, published in January 2007). For the purpose of maintaining the desired storage temperature, a storage tank generally has an apparatus with the aid of which (for example continuously) a portion of the stored liquid monomer phase is or can be withdrawn, conducted through a heat exchanger and then recycled into the storage tank (the process according to the invention can then also be carried out in such a way that the separating operation according to the invention is carried out in the abovementioned withdrawal and/or recycling (for example through filters correspondingly installed in the pipes (for example continuously).

Since the aforementioned polymerization inhibitor systems display their full action normally only in the presence of molecular oxygen (which in turn itself is an inhibitor), the liquid monomer phases are typically stored under a gas atmosphere comprising molecular oxygen (cf., for example, WO 2005/049 543 and U.S. Pat. No. 6,910,511). In other words, the internal volume of the storage tank occupiable by a fluid phase is filled only partly by the liquid monomer phase stored in the storage tank, and the remaining occupiable internal volume of the storage vessel is occupied by a gas phase comprising molecular oxygen. With the aid of mixing apparatus, it is generally ensured that the liquid monomer phase does not become depleted of the molecular oxygen dissolved therein.

The liquid monomer phase remains in the storage tank (in the storage vessel) until it is withdrawn for the purposes of use elsewhere. Such a use consists inter alia in the transport of the liquid monomer phase withdrawn from the storage tank to a consumer.

In general this transport is carried out in the tank of a tank truck (the tank material used is frequently stainless steel). That is to say, the tank is normally transported by a truck (by road) or a rail vehicle (by rail). The capacity (the internal volume occupiable by a liquid medium) of the tank of such a tank truck is generally at least 5 m$^3$, frequently at least 10 m$^3$ and in many cases from 15 to 40 m$^3$ or from 20 to 30 m$^3$; in some cases, its interior is divided into at least 2, generally at least 3 or at least 4, chambers separated completely from one another, each of which is filled independently with liquid monomer phase. The fill volume with liquid monomer phase is typically from approx. 80 to 90% by volume of the internal volume occupiable in each case by a fluid phase. The tank is normally filled by using air.

Frequently, however, the transport is carried out by sea with the aid of a tanker ship (in the tank thereof). The capacity of such a tanker ship normally far exceeds that of the tank of a tank truck). In general, the tank interior of a tanker ship is divided into mutually separated compartments.

It is essential, then, that such a transportation of liquid monomer phase should take place safely. This requires in particular that, during the transportation of the liquid monomer phase, an undesirably free-radical polymerization thereof be very substantially avoided. This not least because a free-radical polymerization takes place exothermally, which especially in the case of unrefrigerated transportation can lead to possibly critical self-heating on the part of the monomer phase being transported (this particularly in the case of comparatively long transportation distances such as for example overseas transports).

At the same time, though, a very low content of free-radical polymerization inhibitor in the transported liquid monomer phase is also desirable.

One reason for this is that the polymerization inhibitors are comparatively costly active ingredients. Secondly, the monomers themselves and/or their later reaction products are frequently capable of reacting with the inhibitors to form intensely colored reaction products, which is generally undesired. Moreover, the polymerization inhibitors normally have an adverse effect (for example on the product quality) in the case of use of the stored liquid monomer phase in free-radical polymerization reactions.

Furthermore, not too high an oxygen content of the gas phase located above the liquid phase in the transport tank is desirable. This is to be attributed to the fact that mixtures of gaseous monomer (the latter evaporates naturally) and molecular oxygen may be explosive (cf. WO 2004/007405, DE-A 10 2004 034 515, WO 2005/049543, Research Disclosure Database Number 513001, published in January 2007 and Research Disclosure Database Number 513002, published in January 2007). Overall, a minimization of the oxygen content in the transport tank is therefore desired. Particularly advantageously, it is below the so-called limiting oxygen concentration (cf. WO 2004/007405), below which explosive behavior of the gas mixture is not possible.

Against the aforementioned background, it was an object of the present invention in particular to provide a process for transporting a liquid monomer phase which has been withdrawn from a storage vessel and whose content of the particular monomer is ≥90% by weight in the tank of a tank truck or of a tanker ship which enables transport with increased safety and optionally reduced inhibitor requirement.

Accordingly, a process has been found for transporting a liquid monomer phase which has been withdrawn from a storage vessel and whose content of the monomer is ≥90% by weight in the tank of a tank truck or of a tanker ship, the monomer being a monomer from the group consisting of acrolein, methacrolein, acrylic acid, methacrylic acid, esters of acrylic acid and an alcohol having from 1 to 12 carbon atoms (preferably from 1 to 8 and more preferably from 1 to 4 carbon atoms) and esters of methacrylic acid and an alcohol having from 1 to 12 carbon atoms (preferably from 1 to 8 and more preferably from 1 to 4 carbon atoms), which comprises subjecting the liquid monomer phase, on the route from the storage vessel into the tank of the tank truck or of the tanker ship, to at least one separating operation to remove at least a portion (preferably at least 25% by weight, better at least 50% by weight, even better at least 75% by weight and at best the entirety (especially of the relative molecular weights specified below)) of polymer of the monomer present dissolved in the liquid monomer phase.

The term "polymer" here shall also encompass oligomer. Primarily, this means polymer/oligomer obtained by (undesired) free-radical polymerization. The wording "polymer present dissolved in the liquid monomer phase" in this document shall comprise both "dissolved in molecular form" and "dissolved in colloidal form", but each only to the extent that the dissolved form is not perceptible visually (i.e. with the naked human eye) in the liquid monomer phase to be stored.

In-house investigations have shown that especially such dissolved polymer (in contrast to macroscopically visible polymer) has a markedly polymerization-promoting activity. This is true in particular in the case of relative molecular weights based on atomic hydrogen of ≥1000, or ≥2000 or ≥3000 of the dissolved polymer.

The undesired formation of such polymer cannot be completely prevented even on storage of the liquid monomer phase at low temperature (≤50° C., better ≤40° C., or ≤30° C., but above the melting point of the monomer phase). Preferred storage temperatures are from 17 to 25° C. Detailed investigations have led to the result that such polymer present in dissolved form in withdrawn liquid monomer phase, in the case of use of withdrawn liquid monomer phase not subjected to a process according to the invention for free-radical polymerizations, has an adverse effect both on the course of the free-radical polymerization and on the quality of the resulting polymer.

The present invention therefore also comprises a process for, for example, free-radical polymerization, which comprises polymerizing (for example with free-radical initiation) liquid monomer phase which has been transported according to the invention, or a mixture thereof with at least monounsaturated (preferably ethylenically unsaturated) compounds other than the transported liquid monomer phase.

That is to say, the process according to the invention can also be applied in particular to liquid monomer phases withdrawn from a storage vessel which are free of solids on visual inspection (i.e. when viewed with the naked human eye).

Useful separating operations for removing polymer present in dissolved form in the liquid monomer phase include especially all mechanical separating operations which are suitable for removing ultrafine solids from liquids. Separating operations particularly suitable in accordance with the invention in this regard are filtering and/or centrifuging separating operations. These include in particular microfiltration, ultrafiltration (nanofiltration) and ultracentrifugation (the bulk densities of oligomerized and/or polymerized monomer are just as sufficiently different from the bulk density of the corresponding monomer as the particular volume expansions; at 25° C. and 1 atm, the bulk density of monomeric acrylic acid is, for example, 1.05 g/cm$^3$, and that of polymerized acrylic acid 1.54 g/cm$^3$; the difference in the bulk density is based in particular on the increased space requirement of the electron cloud of an unsaturated double bond; the oligo- and/or polymerized monomers accumulate on the casing of the ultracentrifuge and can be peeled off continuously therefrom). It will be appreciated that it is also possible to employ chromatographic and osmotic processes as inventive separating operations.

Preferably in accordance with the invention, the (visually imperceptible) polymer present in dissolved form in the liquid monomer phase withdrawn (or to be withdrawn) can be removed from the liquid monomer phase by filtration. The filter materials used may, for example, be filter webs, filter fabrics, fiber layers, sintered materials or bulk material layers (for example of finely divided quartz materials, kieselguhr, activated carbon, zeolites).

In principle, it is possible for the inventive purpose to use, for example, bag filters or candle filters. The inventive filtration task can be achieved both with sewn and fully welded, preferably multilayer filter bags made of different materials. Useful such materials include, for example, stainless steel, polypropylene, cellulose, polyester, metal fabric (stainless steel, for example chromium-nickel stainless steel) and also phenol resin-bound acrylic fibers. A material particularly preferred in accordance with the invention for filters to be used in accordance with the invention (both filter bags and filter candles) is polypropylene. Filter candles usable in accordance with the invention may, however, also be manufactured from activated carbon. In principle, useful filter candles suitable in accordance with the invention include wound candles, melt-blown candles and resin-bound filter candles. According to the invention, both the filter bags and the filter candles may be used both in single and multiple filter casings. Useful casing materials include, for example, polypropylene, stainless steel and carbon steel. Preference is given in accordance with the invention to multiple casings in which up to approx. 40 individual filter bags can be used and which enable flow rates of liquid monomer phase of up to 1000 m$^3$/h. Installation aids or bag downholders improve the correct fit of the filter bags. For example, they reliably prevent "floating" through uncontrolled back pressure. Bursting of the filter bag is likewise prevented. Specific "collars" ensure a perfect and fixed fit of the bag downholder in the filter bag (no fraying or erosion of the filter bag).

Preference is given in accordance with the invention to filter materials (filter media or filter types) whose retention efficiency for particles having a particle diameter of ≤30 µm is at least 70%, preferably at least 80%, more preferably at least 90% or at least 95% and more.

Particular preference is given in the process according to the invention to filter materials (filter media or filter types) whose retention efficiency for particles having a particle diameter of ≤20 µm is at least 70%, preferably at least 80%, more preferably at least 90% or at least 95% and more.

Very particular preference is given in the process according to the invention to filter materials (filter media or filter types) whose retention efficiency for particles having a particle diameter of ≥10 µm is at least 70%, preferably at least 80%, more preferably at least 90% or at least 95% and more.

Even better, in the process according to the invention, filter materials (filter media or filter types) are used whose retention efficiency for particles having a particle diameter of ≥5 µm is at least 70%, preferably at least 80%, more preferably at least 90% or at least 95% and more.

At best, in the process according to the invention, filter materials (filter media or filter types) are used whose retention efficiency for particles having a particle diameter of ≥1 µm is at least 70%, preferably at least 80%, more preferably at least 90% or at least 95% and more.

In general, for the process according to the invention (and also for the withdrawal process still to be explained later in this document), however, filter materials (filter media or filter types) will be used whose retention efficiency for particles having a particle diameter of 0.5 µm is ≤90%, preferably ≤80%. For the process according to the invention, this generally ensures sufficient space-time yields.

The aforementioned percentages are based in each case on the total number of particles of the particular particle size. Moreover, the aforementioned percentages are based on an areal loading of 20 l/(m$^2$·min), water as the carrier medium for the particles, a temperature of 20° C. and a pressure difference of <50 mbar, and test dust according to ISO 12103-1 A3 as the particle type.

The test design is based on the French standard NF 45-303 (cf. Filtration & Separation (Filtr. sep.) ISSN 0015-1882 CODEN FSEPAA Filtration and Separation, 1997, vol. 34, No. 3, pp. 217-223).

All aforementioned properties are fulfilled, for example, by ACCUGAF™ filter bags from Eaton Filtration, LLC., 900 Fairmount Avenue, Elizabeth, N.J. 07207 (USA) of filter models AGF-51, AGF-53, AGF-55, AGF-57 and AGF-59. They are manufactured from melt-blown polypropylene in welded form. They do not comprise any binders, any interface-active substances or any additives (for example tackifying resins). Such filter materials (filter media, filter types) manufactured only from polypropylene are found to be particularly suitable for the process according to the invention, since they incite the liquid monomer phase to be stored in accordance with the invention to undesired free-radical polymerization to a particularly minor degree.

The highest retention efficiencies are achieved using type AGF-51 (at least 90% for particle diameters ≥1 µm). With increasing identifying number, the retention efficiencies decrease. For the AGF-59 type, the retention efficiency for particle diameters of ≥30 µm is, however, still above 90%.

Alternatively, for the process according to the invention, it is also possible to use PROGAF™ or LOFCLEAR™ filter bags from Eaton. The LOFCLEAR filter bags are filter bags composed of multilayer filter material and the PROGAF™ filter bags are filter bags composed of particularly highly efficient filter medium with which effective particle reductions down to the submicron range can be achieved. LOF-CLEAR filter bags are likewise manufactured from 100% polypropylene.

Alternatively, it is possible for a process according to the invention to use the high-performance bag filtes of the "HP" series (especially the HPC, HPB and HPA bag filters) from Pall GmbH, Philipp-Reis-Straβe 6, D-63303 Dreieich. They consist of three polypropylene webs arranged one on top of another; an outer supporting web which ensures a good mechanical strength of the bag filter, the middle active filter web and an inner protective web which functions as a preliminary filter.

Favorable bag filters are those whose pressure difference in the new state in the event of a loading with 10 (preferably with 20) $m^3/h \cdot m^2$ of water at 20° C., is ≤100 mbar. In general, the aforementioned value is, however, ≥5 mbar.

Also suitable in accordance with the invention are candle filters manufactured from polypropylene from FUHR GmbH (D-55270 Klein-Winternheim near Mainz, Am Weinkastell 14). These include in particular the acuraProgard membrane filter candles which are likewise manufactured completely from polypropylene. They have a thermal welded construction and are as a result free of adhesives and binders. Since their filter matrix has a two-layer structure, extremely long lifetimes can be achieved when they are used.

acuraProgrard candle filters are obtainable with retention rates of at least 99.9% for particle diameters of ≥0.2 μm, or ≥0.45 μm, or ≥1 μm, or ≥5 μm, or ≥10 μm or ≥20 μm. They are all suitable for the process according to the invention. The use of the acuraProgrard candle filters with retention rates of at least 99.9% for particle diameters of ≥5 μm are to be emphasized by way of example.

The temperature of the monomer phase to be filtered in accordance with the invention should, especially in the case of use of filter media made from polypropylene, be ≤95° C.

The aforementioned temperature is preferably ≤80° C., more preferably ≤60° C., most preferably ≤40° C. and at best ≤30° C. or ≤25° C. In favorable cases, it may be down to 0° C.

Otherwise, the at least one separating operation of the process according to the invention will generally preferably be performed at temperatures of ≤95° C., preferably ≤80° C., advantageously ≤60° C., particularly advantageously ≤40° C. and at best ≤30° C. or ≤25° C. In favorable cases, it may be down to 0° C. The transport temperatures are likewise preferably low (preferably ≤30° C., typically 17 to 25° C.).

In the case of a filtration to be performed in accordance with the invention as described, differential pressures of from ≥10 mbar to 5 bar may be employed.

The aforementioned differential pressures are preferably ≥20 mbar and ≤3 bar, more preferably ≥20 mbar and ≤2 bar, or ≤1.5 bar. When higher differential pressures are required, the filters should be exchanged. It will be appreciated that useful filter candles for an inventive filtration are also those made from polytetrafluoroethylene (for example the acuraVent AVF filter candles from FUHR GmbH), made from borosilicate fibers (for example the acuraVent AFG-GG filter candles from FUHR GmbH), made from polyether sulfone (for example the acuraFine AFS filter candles from FUHR GmbH), and made from nylon (for example the acuraProgrard filter candles from FUHR GmbH).

It will be appreciated that it is also possible for an inventive filtration to use the acuraBag filter bags from FUHR GmbH, especially those which are manufactured from polypropylene. However, the ACCUFIT® and the ULTRAFIT® filter bags from FUHR GmbH are also suitable in accordance with the invention. Advantageously in accordance with the invention, they are likewise manufactured from polypropylene in a welded design.

In general, filter bags suitable in accordance with the invention are manufactured from several filter layers.

It is advantageous in accordance with the invention when the filter medium used for a process used in accordance with the invention does not expand significantly under the load with liquid monomer phase to be filtered. The aforementioned loading will generally be from 2 to 20 $m^3/(h \cdot m^2)$.

In general, the liquid monomer phase to be filtered, in the case of use of filter bags or filter candles, will be conducted from the inside outward through the filter type. In principle, in the case of use of filter candles, the liquid monomer phase can also be guided from the outside inward.

Typical pore sizes of the filter-active layer of filter materials to be used in accordance with the invention are from 0.1 to 300 μm, preferably from 1 to 200 μm or from 1 to 100 μm and more preferably from 1 to 50 μm or from 1 to 5 μm. As already mentioned, advantageously in accordance with the invention, a plurality of layers (for example 3, or 5, or 7 layers) are employed one on top of another.

The filtration may in principle be practiced as a pressure filtration or as a vacuum filtration. It is preferably performed as a pressure filtration. It will be appreciated that it can also be practiced with centrifugation.

The process according to the invention is also especially suitable when the content of the monomer in the liquid monomer phase is ≥96% by weight or ≥97% by weight, or ≥98% by weight, or ≥99% by weight, or ≥99.5% by weight, or ≥99.7% by weight, or ≥99.9% by weight. The aforementioned and all statements in this document are relevant especially when the monomer is acrylic acid (especially when the liquid monomer phase is acrylic acid (especially when the liquid monomer phase is glacial acrylic acid)).

When a filter type used in accordance with the invention is exhausted, it can be replaced by a fresh filter. Of course, the filter can be configured as an interchangeable filter in accordance with the aim. Washing by means of aqueous alkali metal hydroxide (e.g. potassium hydroxide and/or sodium hydroxide) and subsequent washing to neutrality with pure water allows, in accordance with the invention, exhausted filters to be regenerated. Especially filters manufactured from polypropylene can be incinerated without any problem after their exhaustion.

As active ingredients which inhibit an undesired free-radical polymerization of the monomers present in the liquid monomer phase (for example induced by temperature, light or other spontaneously induced free-radical formation), the liquid monomer phase withdrawn in accordance with the invention may comprise any polymerization inhibitors known for this purpose in the prior art in dissolved form. Polymerization inhibitors used with preference are p-methoxyphenol (MEHQ), phenothiazine, hydroquinones, phenol (e.g. 2,4-dimethyl-6,6-butylphenol), quinones, butylpyrocatechol, diphenylamine, p-phenylenediamines, nitroxyl radicals (e.g. 4-hydroxy-2,2,6,6-tetramethylpiperidine 1-oxyl (4-OH-TEMPO)) and/or nitroso compounds, for example nitrophenols (and also all other polymerization inhibitors mentioned in WO 00/64947).

The inventive procedure enables not only the inhibitor content of the liquid monomer phase to be transported or safe transport but likewise the oxygen content in the gas phase present above the liquid phase in the transport tank to be reduced.

Of course, the required amount of the inhibitor used also depends upon the storage conditions, upon the type of inhibitor, upon the type of monomer and upon the specific purity of the liquid monomer phase. Based on the weight of monomer present in the liquid monomer phase, the inhibitor content is typically ≤400 ppm by weight, frequently ≤220 ppm by weight and often ≤100 ppm by weight.

Appropriately, the procedure in the inventive filling of a tank truck or tanker ship from a storage vessel comprising the liquid monomer phase will be to withdraw the liquid monomer phase to be withdrawn from the storage tank initially as such into a test tank (of course, the separation according to the invention (for example filtration) can also be effected actually directly in the course of the withdrawal (for example by means of a filter disposed in the withdrawal line or at the withdrawal point in the storage vessel)).

From the test tank, the liquid monomer phase withdrawn from the storage tank is then pumped out once or more than once in succession and, for example, recycled back into the test tank each time through a filter system as described above.

When the amount retained in the filter system (for example acuraPrograd candle filter with retention rates of 99.9% for particle diameters of ≥5 μm in a multiple casing) increases insignificantly, if at all, the separating operation is terminated and the monomer phase which has been withdrawn beforehand from the storage tank and is present in the test tank is transferred into the tank of the tank truck or of the tanker ship.

The present application therefore also comprises a process for filling the tank of a tank truck or of a tanker ship with liquid monomer phase which is to be withdrawn from a storage tank, which comprises subjecting the liquid monomer phase, on the route from the storage vessel into the tank of the tank truck or of the tanker ship, to at least one separating operation to remove at least a portion of polymer of the monomer present dissolved in the liquid monomer phase.

The liquid monomer phase can otherwise be stored in the storage vessel, for example as described in WO 2005/049543, U.S. Pat. No. 6,910,511, Research Disclosure Database Number 513002, published in January 2007 and especially Research Disclosure Database Number 513001, published in January 2007.

When the liquid monomer phase to be stored is obtained, for example, by condensation in a rectification column above the feedpoint of the mixture to be separated (in the rectification column) into the rectification column from the vapors ascending within the rectification column, and the liquid monomer phase which is thus obtained by condensation and is to be stored in accordance with the invention is then withdrawn from the rectification column above the aforementioned feed, the condensation can be brought about within the rectification column, for example, by direct cooling and/or indirect cooling. Indirect cooling can be brought about at the top of the column, for example, by conducting the ascending vapor which arrives at the top of the column through an indirect heat exchanger and converting the constituents which are condensable under the conditions of the indirect heat exchange to the liquid phase. A portion of the liquid phase thus obtained is then sent to the storage and the other portion recycled as reflux liquid to the top of the rectification column. This reflux liquid then causes, in the rectification column, actually a direct cooling of the vapor ascending in the rectification column. Constituents which are not condensable in the indirect heat exchanger are conducted out of the rectification column and generally sent to their disposal. The polymerization inhibitor is added directly into the condensate. When the pure product is withdrawn below the top of the column, the phase condensed at the top is normally recycled substantially as reflux liquid into the rectification column. Typically, the reflux liquid comprises added polymerization inhibitor. The pure product withdrawn from the rectification column is thus directly likewise polymerization-inhibited. Of course, the condensation at the top of the column can also be undertaken exclusively by direct cooling. For this purpose, top condensate, once it has been obtained, is admixed with inhibitor, cooled and sprayed at least partly into the top space of the rectification column for the purpose of direct cooling. When the pure product is withdrawn below the top of the column (but above the feedpoint of the mixture to be separated in the rectification column), the cooled total amount of condensate is normally resprayed into the top space. The part of the rectification column comprising separating internals and the condensation space at the top of the column are typically separated from one another by a chimney tray. The reflux liquid is fed to the separating part. The part of the rectification column below the feedpoint into the rectification column is typically referred to as the stripping section, and the part of the rectification column above the feedpoint is typically referred to as the rectifying section of the rectification column.

When the mixture to be separated in the rectification column is fed into the rectification column in liquid form, the separation is a rectification; when the feed is effected in vaporous (or gaseous) form, the separation is a fractional condensation. As separating internals, the rectification column may comprise, for example, trays, structured packings and/or random packings. Exemplary embodiments of a fractional condensation of acrylic acid from the product gas mixture of a heterogeneously catalyzed partial gas phase oxidation of propylene and/or propane are disclosed, for example, by the documents DE-A 199 24 533, DE-A 199 24 532, WO 01/77056, DE-A 101 56 016, DE-A 102 43 625, DE-A 102 23 058, DE-A 102 35 847, WO 2004/035514, WO 00/53560 and DE-A 103 32 758.

When the monomer phase to be stored, is obtained for example, by melting a crystalline phase, this may be the result of a one-stage or of a multistage crystallizative purification of a liquid mixture comprising the relevant monomer (cf., for example, EP-A 616 998). As a result of the action of cold conditions on the liquid mixture, the monomer crystallizes out of the liquid mixture as a crystalline phase.

Frequently, the crystalline phase to be melted is the result of a one-stage crystallization.

It will be appreciated that the phase to be melted may also be the result of a fractional crystallization.

For example, the action of cold conditions on the liquid mixture comprising the monomer may be performed as a layer crystallization (cf. DE-A 26 06 364, EP-A 616 998, EP-A 648 520 and EP-A 776 875). In this method, the crystals are frozen out in the form of continuous, firmly adhering layers on cooled surfaces. The crystals deposited are separated from the remaining residual melt (the mother liquor) through simple flowing-off of the residual melt. In principle, a distinction is drawn between "static" and "dynamic" layer crystallization processes. A characteristic feature of dynamic layer crystallization from liquid mixtures is forced convection of the liquid mixture. This can be effected, for example, by pumped circulation of the liquid mixture through cooled tubes with full flow-through, by applying the liquid mixture as a trickle film to cooled walls (for example according to EP-A 616 998, for example in cooled downpipes) or by introducing inert gas into the liquid mixture or by pulsation.

In the static processes, the liquid mixture is at rest (for example in tube bundles or plate heat exchangers) and is deposited in layer form on the secondary side of the heat exchanger by slowly lowering the temperature. Thereafter, the residual melt (mother liquor) is discharged, more highly contaminated fractions are sweated off from the crystal layer by slowly increasing the temperature and then the pure product is melted off (cf. WO 01/77056).

Generally, the liquid mixture comprising the monomer (normally a solution), from which the monomer is removed by crystallization, comprises added polymerization inhibitor. In the crystallizative deposition of the monomer, it normally crystallizes out essentially free from the polymerization inhibitor. The deposited monomer crystal layer is therefore frequently not melted by heating the secondary side but rather by contacting the monomer crystal layer with a warmed melt of deposited monomer crystal layer which has been melted beforehand, said melt comprising added polymerization inhibitor.

Alternatively, the monomer crystals can also be formed from the liquid mixture comprising the monomer as a suspension crystallization (for example according to the teaching of WO 01/77056, of WO 02/055469 and of WO 03/078378).

In general, a crystal suspension comprising suspended acrylic acid crystals is obtained by cooling the liquid mixture (the liquid solution) which comprises, for example, acrylic acid as a monomer, the acrylic acid crystals having a lower impurity content and the remaining residual melt (mother liquor) a higher impurity content than the liquid starting mixture. The acrylic acid crystals may grow immediately within the suspension and/or be deposited as a layer on a cooled wall, from which they are constantly scraped off and resuspended in the residual melt.

All suspension crystallizers and suspension crystallization processes detailed in WO 01/77056, WO 02/055469 and in WO 03/078378 may be employed. An acrylic acid crystal suspension thus obtained may, for example, have a solids content of from 10 to 50% by weight, frequently from 20 to 40 or 30% by weight.

For the separation of suspension crystals and remaining mother liquor, for example, all separation processes mentioned in the aforementioned WO publications are useful (for example mechanical separating operations such as centrifugation). Preference is given to effecting the separation in a wash column. Advantageously, the wash column is a wash column with forced transport of the deposited, for example, acrylic acid crystals. The wash liquid used is advantageously the melt of, for example, acrylic acid crystals which have been purified (removed) beforehand in the wash column. The wash is normally effected in countercurrent.

All of the aforementioned is true in particular when the wash column is a wash column with forced transport of the, for example, acrylic acid crystals, in particular when it is a hydraulic or a mechanical wash column according to WO 01/77056 and it is operated as detailed there.

A liquid acrylic acid phase to be stored can thus, for example, be obtained as follows. Heterogeneously catalyzed one-stage or two-stage partial oxidation of a $C_3$ precursor of acrylic acid (e.g. propylene, propane or acrolein) generates a product gas mixture comprising acrylic acid. It is conducted into a separating column with separating internals and fractionally condensed ascending therein. Above the feedpoint but below the top of the column, a liquid crude acrylic acid which has ≥95% by weight of acrylic acid and comprises polymerization inhibitor added via the reflux into the separating column is withdrawn from the separating column. Suspension crystallization generates glacial acrylic acid suspension crystals from the crude acrylic acid. This is removed in a wash column (preferably in a hydraulic wash column) from remaining mother liquor using pure crystal melt comprising added polymerization inhibitor as a wash liquid. Contacting of removed pure crystals with the melt of pure crystals which have been removed beforehand which comprises added polymerization inhibitor melts the pure crystals removed and thus generates a liquid acrylic acid phase to be stored (purity generally ≥99.5% by weight).

It will be appreciated that the inventive process can also be applied to liquid monomer phases which have been obtained in different ways and whose content of the monomer is <90% by weight.

The process according to the invention can also be performed in such a way that liquid monomer phase continues to be withdrawn (at best continuously) from the storage tank in the course of storage and is then recycled back into the storage tank, and by this route of withdrawal and recycling is subjected to at least one separating operation to remove at least a portion of polymer of the monomer which is present in dissolved form in the liquid monomer phase and is transferred from the liquid monomer phase stored in this way into the tank of a tank truck or of a tanker ship. In this case, the inventive route of the liquid monomer phase to be transported out of the storage vessel into the tank goes through the storage vessel. It will be appreciated that all inventive variants (or parts of these variants) presented in this document may also be employed in combination.

EXAMPLE AND COMPARATIVE EXAMPLE a) Comparative Example

Fractional condensation of the product gas mixture of a heterogeneously catalyzed partial propylene oxidation generated, as described in example 1 of WO 2004/035514, acrylic acid which comprised 96.9% by weight of acrylic acid and had been polymerization-inhibited with 0.018% by weight of MEHQ, 0.012% by weight of phenothiazine and 0.0004% by weight of molecular oxygen. It was withdrawn from the second collecting tray of the condensation column above the feed of the product gas mixture into the condensation column with a temperature of 100.6° C. and visually free of solids. It was then cooled to 25° C. and two liters are transferred with air into a glass flask having an internal volume of three liters. The glass flask was then stored closed for four months at 20° C. Then 0.5 ml of the stored acrylic acid is withdrawn as such (still visually free of solids) and transferred into a 1.8 ml glass ampoule under an air atmosphere. Subsequently, the ampoule was stored at 120° C. in a forced-air drying cabinet while being rotated, in order to ensure complete mixing. The time t up to complete polymerization of the sample was then recorded. t was 13 h 12 minutes.

b) Example

The procedure of the comparative example was repeated. Upon withdrawal from the glass flask, the entire amount of acrylic acid stored was conducted through an ACCUGAF AGF-51 filter bag disposed. After the filtration had ended, the inner walls of the filter bag had a tacky deposit of polyacrylic acid. 0.5 ml of the filtered acrylic acid was transferred into a 1.8 ml glass ampoule at 20° C. and under an air atmosphere. Subsequently, the ampoule was stored at 120° C. in a forced-air drying cabinet while being rotated, in order to ensure complete mixing. The time t until complete polymerization of the sample was then recorded. t was 20 h 25 minutes.

As the two experiments show, the removal of polymer present in dissolved form (polyacrylic acid present in dissolved form) reduces the tendency of acrylic acid to undesired free-radical polymerization.

U.S. Provisional Patent Application No. 60/896,582, filed Mar. 23, 2007, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

The invention claimed is:

1. A process for transporting a liquid monomer phase which has been withdrawn from a storage vessel into which it has been transferred after removal of undissolved solids contained in it by filtration and in which it has been stored at storage temperatures from 17 to 25° C. and whose content of the monomer is ≥97% by weight in the tank of a tank truck or of a tanker ship, the monomer being a monomer from the group consisting of acrolein, methacrolein, acrylic acid, methacrylic acid, esters of acrylic acid and an alcohol having from 1 to 12 carbon atoms and esters of methacrylic acid and an alcohol having from 1 to 12 carbon atoms, which comprises subjecting the liquid monomer phase, on the route from the storage vessel into the tank of the tank truck or of the tanker ship, to at least one separating operation to remove at least a portion of polymer of the monomer present dissolved in the liquid monomer phase, wherein the at least one separating operation is a filtration in which the degree of retention efficiency of the filter medium used for particles having a particle diameter of ≥30 µm is at least 90%.

2. The process according to claim 1, wherein the internal volume of the storage vessel occupiable by a fluid phase is from 100 m³ to 10 000 m³.

3. The process according to any one of claims 1 and 2, wherein the storage vessel has a device with the aid of which a portion of the stored liquid monomer phase can be withdrawn, conducted through a heat exchanger and then recycled into the storage tank.

4. The process according to any one of claims 1 and 2, wherein the liquid monomer phase in the storage vessel is stored under an atmosphere comprising molecular oxygen.

5. The process according to any one of claims 1 and 2, wherein the liquid monomer phase comprises dissolved p-methoxyphenol and/or phenothiazine.

6. The process according to any one of claims 1 and 2, wherein the filter medium used has been manufactured from polypropylene.

7. The process according to any of claims 1 and 2, wherein the filter medium has been manufactured from stainless steel.

8. A process for transporting a liquid monomer phase which has been withdrawn from a storage vessel into which it has been transferred after removal of undissolved solids contained in it by filtration and in which it has been stored at storage temperatures from 17 to 25° C. and whose content of the monomer is ≥97% by weight in the tank of a tank truck or of a tanker ship, the monomer being a monomer from the group consisting of acrolein, methacrolein, acrylic acid, methacrylic acid, esters of acrylic acid and an alcohol having from 1 to 12 carbon atoms and esters of methacrylic acid and an alcohol having from 1 to 12 carbon atoms, which comprises subjecting the liquid monomer phase, on the route from the storage vessel into the tank of the tank truck or of the tanker ship, to at least one separating operation to remove at least a portion of polymer of the monomer present dissolved in the liquid monomer phase, wherein the at least one separating operation is a filtration in which the degree of retention efficiency of the filter medium used for particles having a particle diameter of ≥10 µm is at least 90%.

9. The process according to any one of claims 1 and 2, wherein the at least one separating operation is performed at a temperature of ≤50° C.

10. The process according to any one of claims 1 and 2, wherein the internal volume of the tank of the tank truck or tanker ship occupiable by a fluid medium is 5 m³.

11. The process according to any one of claims 1 and 2, wherein the liquid monomer phase is glacial acrylic acid whose acrylic acid content is ≥99% by weight.

12. A process for free-radical polymerization, which comprises polymerizing transported liquid monomer phase by a process according to any one of claims 1 and 2 or a mixture thereof with at least monounsaturated compounds other than the transported liquid monomer phase.

13. A process for filling the tank of a tank truck or of a tanker ship with liquid monomer phase which is to be withdrawn from a storage tank into which it has been transferred after removal of undissolved solids contained in it by filtration and in which it has been stored at storage temperatures from 17 to 25° C. and whose content of the monomer is ≥97% by weight, the monomer being a monomer from the group consisting of acrolein, methacrolein, acrylic acid, methacrylic acid, esters of acrylic acid and an alcohol having from 1 to 12 carbon atoms and esters of methacrylic acid and an alcohol having from 1 to 12 carbon atoms, which comprises subjecting the liquid monomer phase, on the route from the storage vessel into the tank of the tank truck or of the tanker ship, to at least one separating operation to remove at least a portion of polymer of the monomer present dissolved in the liquid monomer phase, wherein the at least one separating operation is a filtration in which the degree of retention efficiency of the filter medium used for particles having a particle diameter of ≥30 µm is at least 90%.

* * * * *